United States Patent
Yee et al.

(10) Patent No.: US 10,631,401 B2
(45) Date of Patent: Apr. 21, 2020

(54) MODULAR DEFORMABLE PLATFORM

(71) Applicants: Robert Bosch GmbH, Stuttgart (DE); Seow Yuen Yee, Mountain View, CA (US); Gary Yama, Mountain View, CA (US); Bongsang Kim, Mountain View, CA (US); Ashwin Samarao, Sunnyvale, CA (US)

(72) Inventors: Seow Yuen Yee, Mountain View, CA (US); Gary Yama, Mountain View, CA (US); Bongsang Kim, Mountain View, CA (US); Ashwin Samarao, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/535,293

(22) PCT Filed: Dec. 14, 2015

(86) PCT No.: PCT/US2015/065579
§ 371 (c)(1),
(2) Date: Jun. 12, 2017

(87) PCT Pub. No.: WO2016/100218
PCT Pub. Date: Jun. 23, 2016

(65) Prior Publication Data
US 2017/0367172 A1    Dec. 21, 2017

Related U.S. Application Data

(60) Provisional application No. 62/091,690, filed on Dec. 15, 2014.

(51) Int. Cl.
*H05K 1/02* (2006.01)
*A61B 5/00* (2006.01)
(Continued)

(52) U.S. Cl.
CPC ............... *H05K 1/028* (2013.01); *A61B 5/01* (2013.01); *A61B 5/11* (2013.01); *A61B 5/4519* (2013.01);
(Continued)

(58) Field of Classification Search
CPC ........ H05K 1/118; H05K 1/189; H05K 1/141; H05K 1/02; H05K 1/028; H05K 1/0393; H05K 3/00; H05K 3/28; H05K 3/30
(Continued)

(56) References Cited

U.S. PATENT DOCUMENTS 3,903,667 A * 9/1975 Zetlin ...................... E04B 5/43
                                                              52/220.3
5,205,091 A * 4/1993 Brown .................. E04F 15/024
                                                              52/126.6
(Continued)

FOREIGN PATENT DOCUMENTS

| JP | 2005-026340 A | 1/2005 |
| JP | 2006-269559 A | 10/2006 |
| KR | 10-2014-0091978 A | 7/2014 |

OTHER PUBLICATIONS

International Search Report corresponding to PCT Application No. PCT/US2015/065579, dated Apr. 19, 2016 (3 pages).

*Primary Examiner* — Tuan T Dinh
(74) *Attorney, Agent, or Firm* — Maginot, Moore & Beck LLP

(57) ABSTRACT

A modular deformable electronics platform is attachable to a deformable surface, such as skin. The platform is tolerant to surface deformation and motion, can flex in and out of a plane of the platform without hindering operability of electrical components included on the platform, and is formed via arrangement of discrete flexible tiles, with corners of adjacent tiles connected by a flexible connection material so that individual tiles can translate and rotate relative to each (Continued)

other. Interconnects disposed on bases of separate tiles electrically connect adjacent tiles via their connected corners, and electrically connect components disposed on different tiles. Each pair of adjacent corner connections defines an axis about which at least a portion of the platform can flex without deformation and without hindering connections between tiles. The flexible material and/or bases of the tiles can include Parylene.

11 Claims, 6 Drawing Sheets

(51) Int. Cl.
| | |
|---|---|
| H05K 1/03 | (2006.01) |
| H05K 1/14 | (2006.01) |
| H05K 1/18 | (2006.01) |
| H05K 3/00 | (2006.01) |
| H05K 3/28 | (2006.01) |
| A61B 5/01 | (2006.01) |
| A61B 5/11 | (2006.01) |
| H05K 1/11 | (2006.01) |
| H05K 3/30 | (2006.01) |
| H05K 3/12 | (2006.01) |

(52) U.S. Cl.
CPC .......... *A61B 5/4528* (2013.01); *A61B 5/4542* (2013.01); *A61B 5/6833* (2013.01); *H05K 1/0278* (2013.01); *H05K 1/0393* (2013.01); *H05K 1/118* (2013.01); *H05K 1/148* (2013.01); *H05K 1/189* (2013.01); *H05K 3/005* (2013.01); *H05K 3/0052* (2013.01); *H05K 3/0097* (2013.01); *H05K 3/281* (2013.01); *H05K 3/285* (2013.01); *H05K 3/30* (2013.01); *A61B 5/0022* (2013.01); *A61B 2560/0242* (2013.01); *A61B 2560/0412* (2013.01); *A61B 2562/0204* (2013.01); *A61B 2562/028* (2013.01); *A61B 2562/029* (2013.01); *A61B 2562/0247* (2013.01); *A61B 2562/0271* (2013.01); *A61B 2562/066* (2013.01); *A61B 2562/12* (2013.01); *A61B 2562/164* (2013.01); *H01L 2924/0002* (2013.01); *H05K 1/0281* (2013.01); *H05K 3/0058* (2013.01); *H05K 3/1216* (2013.01); *H05K 2201/053* (2013.01); *H05K 2201/09063* (2013.01); *H05K 2201/10037* (2013.01); *H05K 2201/10121* (2013.01); *H05K 2201/10151* (2013.01); *H05K 2203/1453* (2013.01); *H05K 2203/1545* (2013.01)

(58) Field of Classification Search
USPC ........................ 361/749–750, 777–785, 803; 174/250–261
See application file for complete search history.

(56) References Cited

U.S. PATENT DOCUMENTS

| | | | | |
|---|---|---|---|---|
| 5,764,413 | A * | 6/1998 | Smith | G02B 5/124 264/2.5 |
| 6,306,318 | B1 * | 10/2001 | Ricciardelli | B29C 45/0005 264/37.32 |
| 6,460,303 | B1 * | 10/2002 | Pacione | A47G 27/025 428/100 |
| 8,859,980 | B2 * | 10/2014 | Prieels | A61N 5/1075 250/374 |
| 2001/0050176 | A1 * | 12/2001 | Gebhardt | G01R 33/28 174/68.1 |
| 2002/0023394 | A1 * | 2/2002 | McGinnis | E02D 27/42 52/79.1 |
| 2005/0116667 | A1 * | 6/2005 | Mueller | E04F 13/08 315/312 |
| 2007/0013269 | A1 * | 1/2007 | Huang | B06B 1/0292 310/334 |
| 2009/0160289 | A1 | 6/2009 | Wilser et al. | |
| 2010/0139184 | A1 * | 6/2010 | Williams | E04D 11/002 52/173.3 |
| 2012/0320581 | A1 * | 12/2012 | Rogers | H01L 24/24 362/235 |
| 2013/0026380 | A1 * | 1/2013 | Tkaczyk | G01T 1/2928 250/370.13 |
| 2013/0168228 | A1 * | 7/2013 | Ozin | B01J 35/004 204/157.9 |
| 2013/0304019 | A1 * | 11/2013 | Cooper | A61N 5/062 604/501 |
| 2013/0333094 | A1 | 12/2013 | Rogers et al. | |
| 2014/0227934 | A1 * | 8/2014 | Rudisill | A63H 33/046 446/92 |

* cited by examiner

MODULAR DEFORMABLE PLATFORM

RELATED APPLICATION

This application is a 35 U.S.C. § 371 National Stage Application of PCT/US2015/065579, filed on Dec. 14, 2015, which claims priority to U.S. Provisional Application No. 62/091,690 filed on Dec. 15, 2014, entitled "MODULAR DEFORMABLE PLATFORM". The disclosures of the above-identified patent applications are both incorporated by reference herein in their entirety.

TECHNICAL FIELD

This disclosure relates generally to flexible electronics and, more particularly, to modular flexible and deformable devices.

BACKGROUND

Flexible electronics have a wide variety of potential applications that include communications, medical sensing, diagnostics, entertainment, analytics, and many other uses. Devices, sensors, indicators, and other circuitry can be disposed on a flexible substrate that is configured to conform to irregular or dynamic three-dimensional surfaces. Such devices can be adapted for use in wearable devices, skin-adhering devices, or devices not optimal for mounting a rigid circuit such as tires, flexible displays, fabrics, or other surfaces subject to deformation, vibration, or other forces.

Flexible devices have been produced that generally include a flexible substrate patch. Adhesive material can be included on one side of the patch for mounting on a surface such as fabric or skin, and electrical components can be included in or on the substrate patch. In another example, a patch can be attached with a tape, or held in place via a restraining body. While such devices can be configured to bend in and out of a plane of the substrate patch in response to motion of surface, such bending does not optimally account for the complex forces and motions resulting from three-dimensional surface motion and deformation.

For example, such patches generally have a limited range of motion, and are generally not adapted to compensate for deformation, and thus have a relatively limited stretchability. Delamination between the device and the surface can occur in regions where the device is unable to comport with the three-dimensional motion. This can lead to detachment of the device from the surface, interruption impedance, or damage of operation of the device, and other undesirable outcomes. An example of this phenomenon is easily illustrated with a customary adhesive bandage. Not only does the bandage lose adherence over time due to relative motion between a user's skin and the adhesive surface of the bandage, but also, the limited stretchability of the bandage can cause the user discomfort. The user may feel their skin being pulled by the bandage when they move a nearby joint that results in the deformation of nearby skin.

Techniques have been proposed for decreasing delamination between a flexible device and a surface. In one example, U.S. Pat. No. 8,520,399, issued Aug. 27, 2013, describes cuts or perforations in the substrate that are arranged to increase a stretchability of the substrate. Where a definition or use of a term in a reference is inconsistent or contrary to the definition of that term provided herein, the definition of that term provided herein applies herein and the definition of that term in the reference does not apply. In another example, U.S. Pat. No. 8,389,862 describes devices with islands of rigid integrated circuits with edges separated and connected by deformable interconnects, and which are disposed on a continuous sheet of an elastomeric substrate. These approaches have a limited applicability, and can add complexity and expense to both the production of flexible devices, and to the flexible devices themselves.

What is needed, therefore, is a flexible device that is optimized for connection to irregular and dynamic surfaces. A flexible device that is also configured to deform to compensate for complex three-dimensional motion, while maintaining a relatively simple design and fabrication process, would also be beneficial.

SUMMARY

In order to facilitate the operation of electronics on deformable surface, an electronics platform according to this disclosure is configured to be modular and deformable. In an exemplary embodiment, the platform includes a plurality of discrete flexible tiles, a plurality of flexible corner connections, and at least one electrical component. Each tile defines at least one corner, and the flexible corner connections connect corners of adjacent tiles, and enable tiles to at least one of translate and rotate relative to each other while maintaining connections therebetween. The at least one electrical component is disposed on one of the tiles.

In an embodiment, the platform further includes at least one further electrical component disposed another of the tiles, and also includes a plurality of interconnects. The plurality of interconnects are disposed on the plurality of tiles such that the at least one electrical component is electrically in communication with the at least one further electrical component. The corner connections are positioned such that each flexible corner connection covers a respective set of adjacent interconnects.

In another embodiment, each tile includes a base, and each interconnect is disposed on the base of a respective tile in a region of the at least one corner of that tile, such that interconnects of adjacent tiles are configured to electrically connect the adjacent tiles.

In a further embodiment, at least one of the base and the flexible corner connections includes a Parylene.

In one embodiment, the at least one electrical component includes at least one of a sensor, a battery, an indicator, an antenna, a photocell, and an integrated circuit. In an embodiment, the sensor is configured to detect at least one of temperature, humidity, motion, pressure, toxicity, sound, vibrations, and a medical condition of a user.

In another embodiment, a first subset of the plurality of discrete tiles are extension tiles that do not include an electrical component, the extension tiles distributed radially around a second subset of the plurality of discrete tiles that has at least one electrical component.

In one embodiment, the plurality of discrete tiles defines gaps between edges of adjacent tiles. The gaps are configured to enable the platform to flex into and out of a plane of the platform.

In a further embodiment, each pair of adjacent corner connections defines an axis about which at least a portion of the platform is configured to flex without deformation, and without disturbing the operability of electrical components or the electrical connections between different tiles.

In an embodiment, the plurality of flexible corner connections are formed by a passivation layer disposed over the plurality of tiles. The passivation layer can be separated via the gaps, such as via a punch-out process, into the plurality of flexible corner connections and a discrete layer over each tile.

In order to facilitate an exemplary embodiment of the production of a modular deformable electronics platform according to this disclosure includes disposing a plurality of interconnects on a substrate at locations corresponding to an arrangement of discrete tiles. At least one die corresponding to at least one electrical component is then disposed on the substrate at a location corresponding to one of the discrete tiles so as to be electrically connected to the plurality of interconnects. A layer of flexible material is then applied over the plurality of interconnects and the at least one die on the substrate. This intermediate assembly is then formed into discrete tiles with interconnected corners via a punching-out process. Regions of the flexible material and the substrate that correspond to gaps between edges of the discrete tiles in the tile arrangement are punched out. The resulting discrete tiles are electrically connected via the plurality of interconnects, and have corners, whereby the corners of adjacent tiles are connected via the flexible material. A remainder of the substrate and flexible material surrounding the arrangement of discrete tiles is then removed in order to form the modular deformable electronics platform.

In an embodiment, the method further includes applying an adhesive to a side of the substrate facing away from the flexible material. In one embodiment, a protective removable backing is disposed over the adhesive.

In a further embodiment, the gaps are configured to enable the modular deformable electronics platform to flex in and out of a plane of the modular deformable electronics platform.

DETAILED DESCRIPTION

For the purposes of promoting an understanding of the principles of the embodiments described herein, reference is now made to the drawings and descriptions in the following written specification. No limitation to the scope of the subject matter is intended by the references. This disclosure also includes any alterations and modifications to the illustrated embodiments and includes further applications of the principles of the described embodiments as would normally occur to one skilled in the art to which this document pertains.

Figure 1:
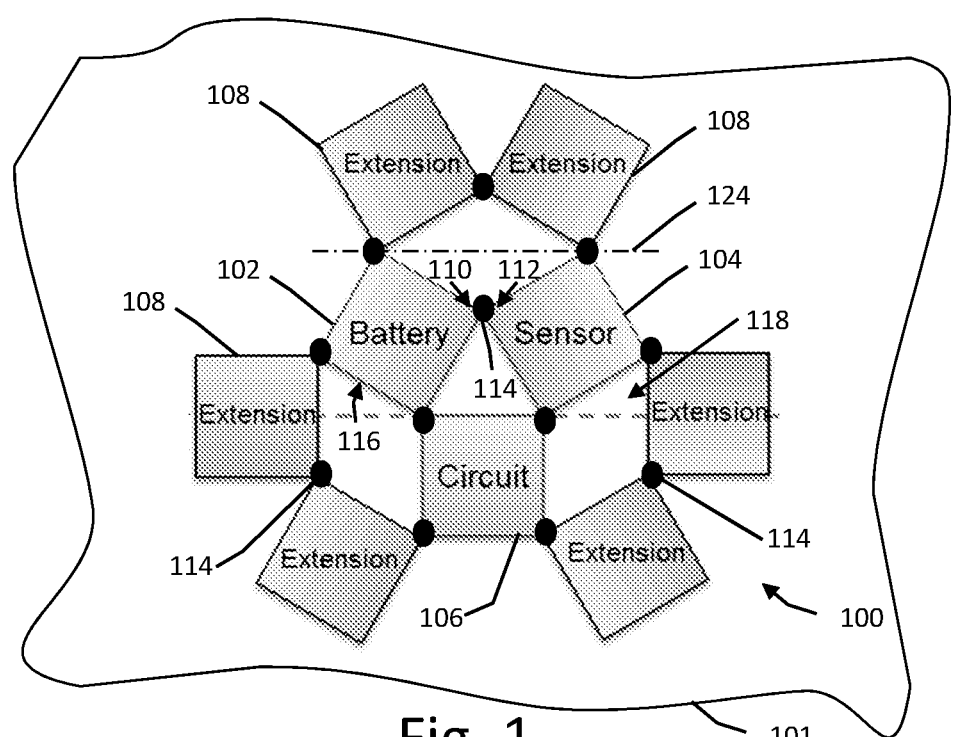
FIG. 1 is a schematic top view of an exemplary embodiment of a modular flexible deformable platform according to the disclosure.

FIG. 1 illustrates a top view of an exemplary embodiment of a modular flexible deformable platform 100 that is formed from a plurality of interconnected tiles and disposed on a surface 101. While not illustrated in detail, it should be understood that the surface 101 can be irregular, and can exhibit dynamic motion and deformation. It should also be understood that the surface 101 is not a part of the platform 100.

In this embodiment, the platform 100 includes a battery tile 102, a sensor tile, 104, a circuit tile 106, and a plurality of extension tiles 108. Tile connections between adjacent tiles in the platform 100, such as a corner 110 of the battery 102 and corner 112 of the sensor tile 104, are formed by corner connections 114. Although connected at corners, edges 116 of adjacent tiles are separated by respective gaps 118.

In one embodiment, tiles in the platform 100 have a diameter of 1 mm or less. While FIG. 1 illustrates tiles as being a similar size, it should be understood that in other embodiments, different tiles can be different sizes. Furthermore, larger or smaller tiles may be desirable for different reasons. In one embodiment, a larger tile is desirable to enable better adherence to the surface 101 or to enable emplacement of a larger component, such as a photocell. In another embodiment, smaller tiles are desirable to enable better tolerance for deformation of the surface 101.

Figure 2:
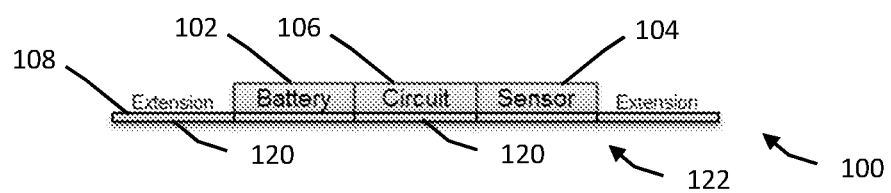
FIG. 2 is a front view of a modular flexible deformable platform.

FIG. 2 illustrates a front view of the platform 100. Each tile in the platform 100 includes a base 120. The base 120 of different tiles is configured to include interconnects, i.e., printed circuit connections (not shown) configured to electrically connect adjacent tiles. In one embodiment, the base 120 is formed from a thin film material, and is less than a millimeter thick, or more particularly, has a thickness on the order of micrometers. Component tiles, such as the battery tile 102, sensor tile 104, and circuit tile 106, further include a corresponding component, i.e., a battery 102, sensor 104, and circuit 106, disposed on a respective base 120. A "component tile" generally means a tile where at least one component is disposed on the respective base 120. Tiles without a component are referred to as extension tiles 108. The interconnect of a respective base 120 is configured to electrically connect with a component disposed thereon to enable the component to be electrically connected to other tiles in the platform 100.

In other embodiments, additional component tiles may include other components disposed on respective bases. Moreover, in some embodiments, multiple components, such as a battery and a sensor, for example, are disposed on a single tile. Other types of components include but are not limited to indicators, transmitters, receivers, and photocells. Components can be of various sizes, and may or may not take up all of the area of a tile. Components can have a variety of thicknesses. In one embodiment, a battery component includes a thin film battery having a thickness in the range of micrometers. In another embodiment, an indicator component includes an indicator having a thickness of approximately half a millimeter. In general, thinner components are preferred since they are generally more tolerant of deformation, and are less noticeable when, for example, the platform 100 is attached to skin of a user.

The base 120 of a tile can be formed from any desired flexible substrate. In this embodiment, the base 120 is formed from a Parylene material. As used herein, "Parylene" means a polymerization of para-xylylene (poly(p-xylylene)) or its substituted derivatives. In some embodiments, a deposited Parylene may be passive or reactive. In at least one embodiment, a deposited Parylene may be halogenated, such as with Fluorine, Chlorine, or Bromine. In some embodiments, the Parylene is a Parylene variant such as Parylene HT, Parylene A, Parylene AM, Parylene AF-4, Parylene N, Parylene C, Parylene D, or Parylene X polymers.

In one embodiment, material for forming the base 120 of the tiles is selected to enable an electrostatic adhesion, i.e., electroadhesion, between the platform 100 and the surface 101 (FIG. 1). Generally, electroadhesion occurs when a buildup of static electricity results in an attractive electrostatic force between to objects. The extension tiles 108 advantageously have a high surface area to volume ratio, and thereby enable electroadhesion to the surface 101. In another embodiment, a rear side 122 of the platform 100 is coated with an adhesive material configured to adhere the platform 100 to the surface 101. Any type of desired adhesive or glue is acceptable. In one embodiment, adhesive is applied only to a portion of each tile to optimize the deformation tolerance of the platform 100, as described in further detail below.

Although illustrated in FIG. 1 as having substantially square shapes, tiles in the platform can have any shape that includes corners that enable forming the corner connections 114. Tiles can be triangles, rectangles, octagons, other regular polygons, irregular polygons, or other irregular shapes that include substantially angular corners. In one embodiment, all tiles have the same shape. In another embodiment, different tiles have different shapes.

Corner connections 114 join two opposing corners of adjacent tiles, and are configured to provide a flexible physical connection between adjacent tiles. Corner connections 114 are formed, for example, by any desired flexible material. In one embodiment, the corner connections are formed from material that can be printed over an arrangement of tiles via a printing device, with material in regions of the gaps 118 being removed. One example of a type of flexible connection material is a polymer, but other types of flexible material are also contemplated. In this embodiment, the corner connections 114 include a Parylene material, and are formed between tiles by applying a layer of corner connection material over an entirety of the platform, and punching out regions corresponding to the gaps 116. In this embodiment, the component tiles 102-106 and extension tiles 108 are additionally coated with a layer of the corner connection material, which can also be configured to operate as a passivation layer or protective coating.

Figure 3:
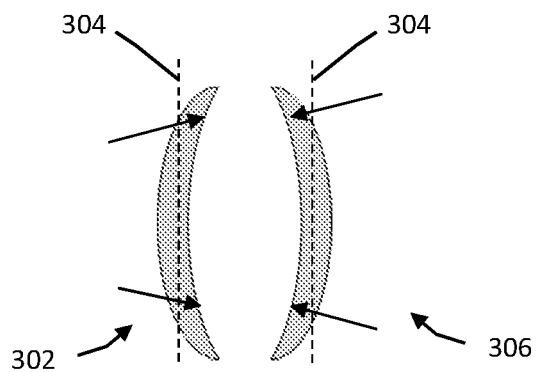
FIG. 3 is a side view of a modular flexible deformable platform.

In FIG. 1, the platform 100 is illustrated as having the component tiles 102, 104, and 106 connected in a central triangle formation, with two extension tiles 108 extending radially outward from each component tile 102, 104, and 106. The tiles are positioned and connected to each other in an arrangement that enables the platform 100 to flex into and out of a plane of the platform 100. FIG. 3 includes illustrations of exemplary flexion 302 into the plane 304 of the platform 100, and exemplary flexion 306 out of the plane 304 of the platform 100 from the perspective of side view B in FIG. 1. It should be understood that the arrangement also enables similar flexion in directions orthogonal to the perspective of side view B.

Even though the platform 100 is enabled to flex in and out of the plane 304 of the platform 100, flexing or deformation of the surface 101 will result in at least some relative motion between portions of the surface 101 and the platform. In one embodiment, if the surface 101 curls down into the plane of the platform 100 as shown in 302 of FIG. 3, the adhesion of the platform 100 to the surface 101 will act to stretch the platform 100. Similarly, if the surface curls upwards out of the plane of the platform 100 as shown in 306 of FIG. 3, the adhesion forces will act to compress the platform 100. In conventional platforms, these stretching and compressing forces are delaminating forces that act to separate the platform from the surface. Such forces generally concentrate along a break region that exhibits the highest relative motion with the surface 101. If the delamination forces overcome the adhesion forces, the platform 100 will delaminate, and can tear, rip, form wrinkles of un-adhered platform, or separate from the surface 100.

However, in this embodiment, the delamination forces are distributed amongst the discrete tiles, and are thus decreased. Rather than being attached to the surface 101 over an entirety of the platform 101, as in a conventional patch, each tile in the platform 100 is discretely attached to the surface 101 via a respective base 120. Because attachment is distributed amongst different bases 120, deformation and delamination forces act separately on each base 120, rather than concentrating at one break region on a patch. Further, the flexible material of the corner connections 114 and the gaps 116 enable individual tiles to translate and rotate relative to each other. In this way, the discrete tiles act at least in part like a plurality of separate pin connections which are impacted less by deformation of the surface in that relative motion between tiles can compensate for a portion of the deformation. Localizing an adhesive on only a portion of the tiles can further improve this behavior, as portions of the tiles are free to move relative to the surface 101, and as a result less of the base 120 deforms.

Further, an imaginary line between each pair of two corner connections 114 defines an axis about which at least a portion of the platform 100 can flex without deforming. In one embodiment, the corner connection between the battery 102 and the extension tile 108 effectively forms a hinge 124 with the corner connection between the sensor 104 and the opposing extension tile 108 that enables the extension tiles flex into our out of the plane of the platform 100 without causing a deformation in the platform 100.

While irregular deformation of the surface 101 may not act along such a hinge line, such hinge lines will act to distribute, reduce, and separate deformation forces. Because the deformation forces are distributed, the force exhibited on any particular tile is decreased relative to when the deformation forces acting on an entire patch concentrate at a single break region.

In this embodiment, the extension tiles 108 extending radially from each component tile are connected to an adjacent extension tile extending from the other component tiles. This arrangement can increase the strength of the platform 100 relative to embodiments where the extensions are not connected, but may limit the amount of relative motion between tiles, and thus limit the platform 100's tolerance to deformation of the surface 101. Other arrangements, such as those described in more detail below, are also contemplated.

Figure 4:
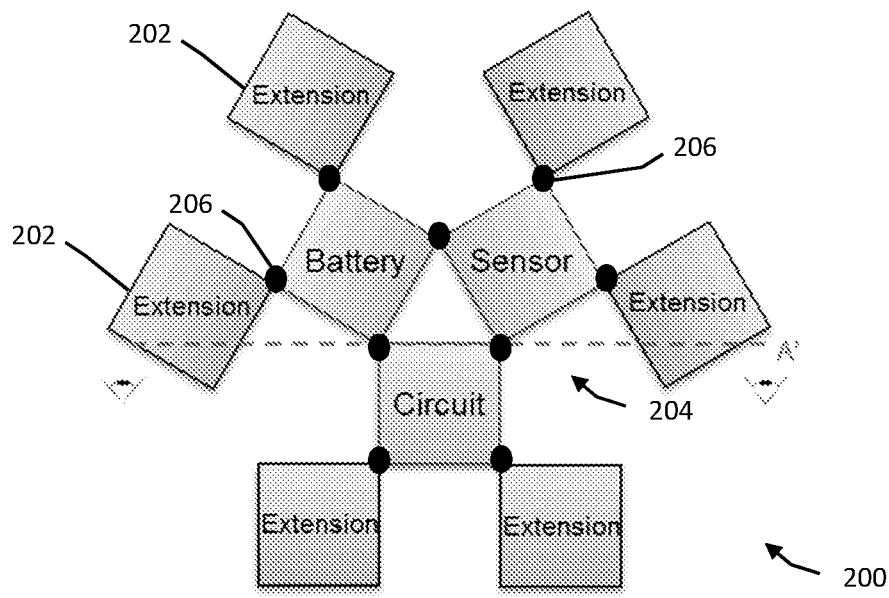
FIGS. 4 and 5 are different embodiments of modular flexible deformable platforms according to the disclosure.

FIG. 4 illustrates another exemplary embodiment of a platform 200. In the platform 200, the extension tiles 202 extending radially from each component tile in the central triangle formation 204 are not connected to extension tiles extending from adjacent component tiles such that each extension tile 202 has only a single corner connection 206 with a component tile. This arrangement of tiles enables a greater range of relative motion of individual tiles compared to the arrangement illustrated in FIG. 1, and also facilitates solid adhesion between the platform 200 and a surface.

Figure 5:
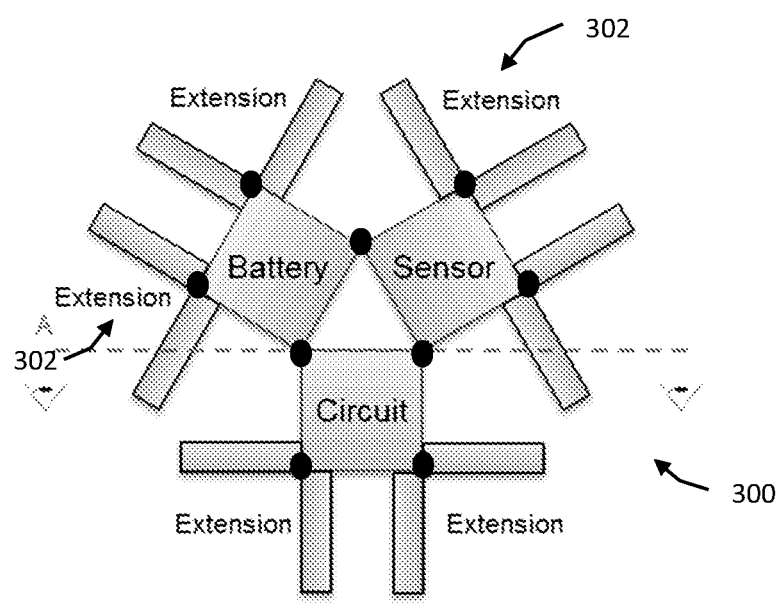

FIG. 5 illustrates an exemplary embodiment of a platform 300 where the square-shaped extension tiles 202 in FIG. 4 are replaced in each case with two orthogonally opposed extension tiles 302 that have a substantially rectangular shape. This arrangement is configured to optimize the adhesion of the extension tiles 302 to a surface with the platform 300's tolerance for defamation. The decrease in total surface area of the platform 300 increases the tolerance of deformation, and the orthogonal orientation of the pairs of extension tiles 302 facilitate adhesion to the surface.

Figure 6:
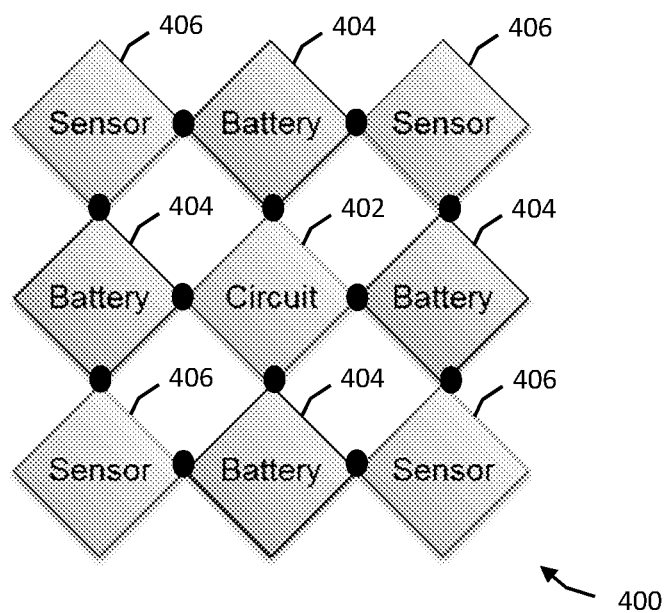
FIG. 6 is a schematic top view of another exemplary embodiment of a modular flexible deformable platform according to the disclosure.

Some arrangements of tiles have different tolerances for flexing and deformation than others. FIG. 6 illustrates a plurality of tiles arranged in a checkerboard configuration 400. While FIG. 6 illustrates an arrangement of a central circuit tile 402 connected to four orthogonal battery tiles 404, with each two adjacent battery tiles joined via a respective sensor tile 406, other checkerboard arrangement with different tiles are also contemplated. In one embodiment, one or more components in the configuration 400 are replaced with an extension tile or a different component tile. In other embodiments, the checkerboard configuration includes a fewer or greater amount of columns or rows of tiles.

Figure 7:
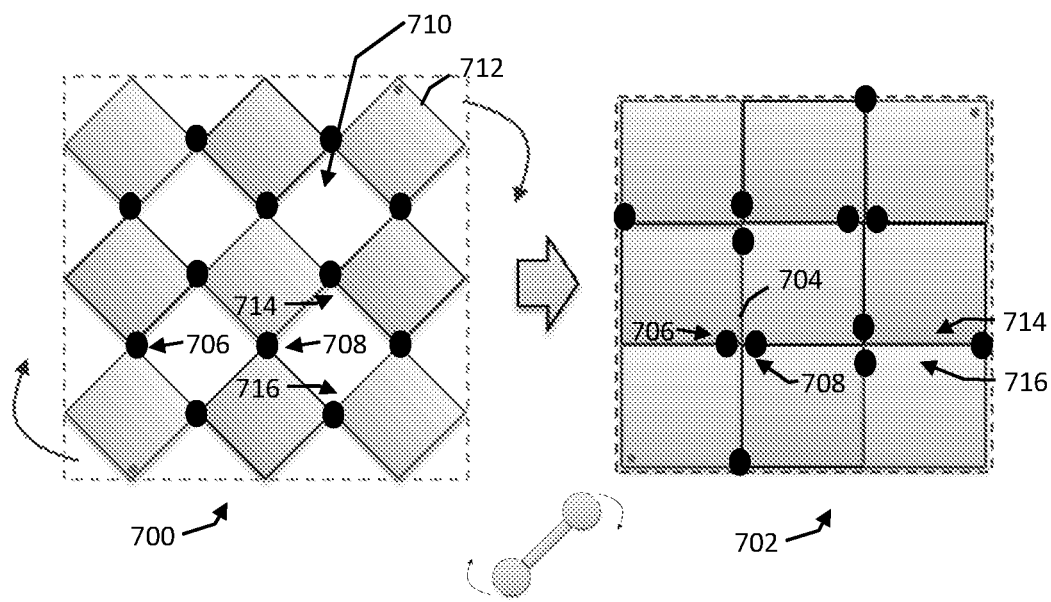
FIGS. 7 and 8 illustrate different exemplary deformations of the modular flexible deformable platform of FIG. 6.
Figure 8:
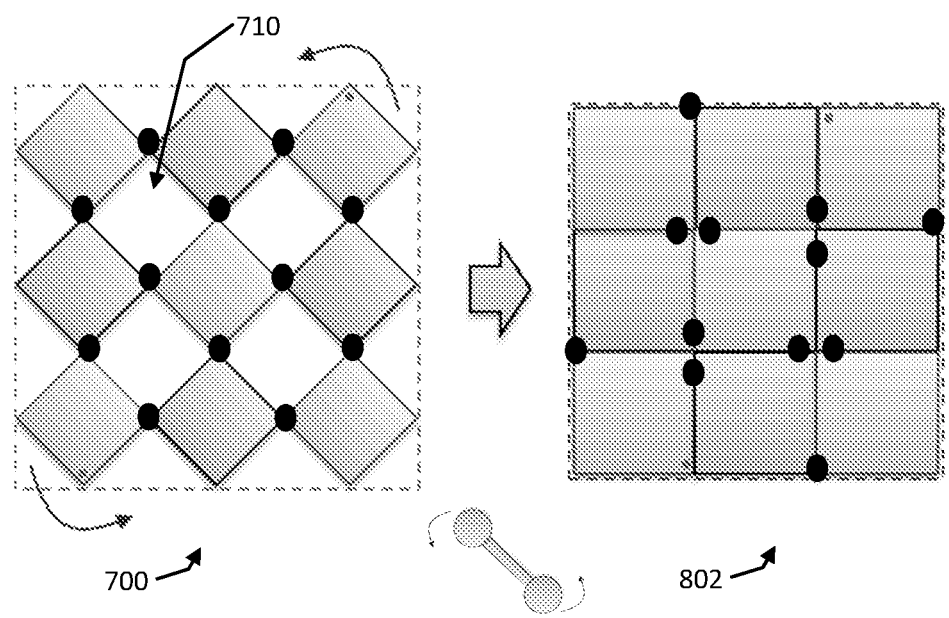

The checkerboard configuration 400 is configured to deform in both footprint and orientation in response to torsional forces. FIGS. 7 and 8 illustrate how torsional forces in a clockwise and counterclockwise direction, respectively, operate to move a checkerboard configuration from an extended position 700 to condensed positions 702 and 802 respectively. As illustrated in FIG. 7, tiles on a corner of the configuration include two corner connections to two adjacent tiles, tiles on a side of the configuration include three corner connections, one to an interior tile and one to tiles on each side, and tiles that are internal and not on a side or corner have four corner connections to the surrounding tiles. This relationship is maintained when additional rows or columns are included.

The torsional force causes the corner tile 712 to rotate clockwise. The corner connections of the tile 712 cause the connected tiles to rotate counterclockwise. In this way adjacent tiles alternatingly move clockwise or counterclockwise between the position 700 to the position 702. It should be understood that while sides 714 and 716 move together when the configuration 400 moves from the extended position 700 to the condensed position 702, the sides 714, 716 are not connected. In FIG. 8, with the torsional forces reversed, inverse rotations occur to move the configuration from the position 700 to the position 802. It should be understood that, since the gaps 710 are not present in the condensed positions 702, 802, that the condensed positions 702, 802 have a smaller total footprint than the extended position 700.

Figure 9:
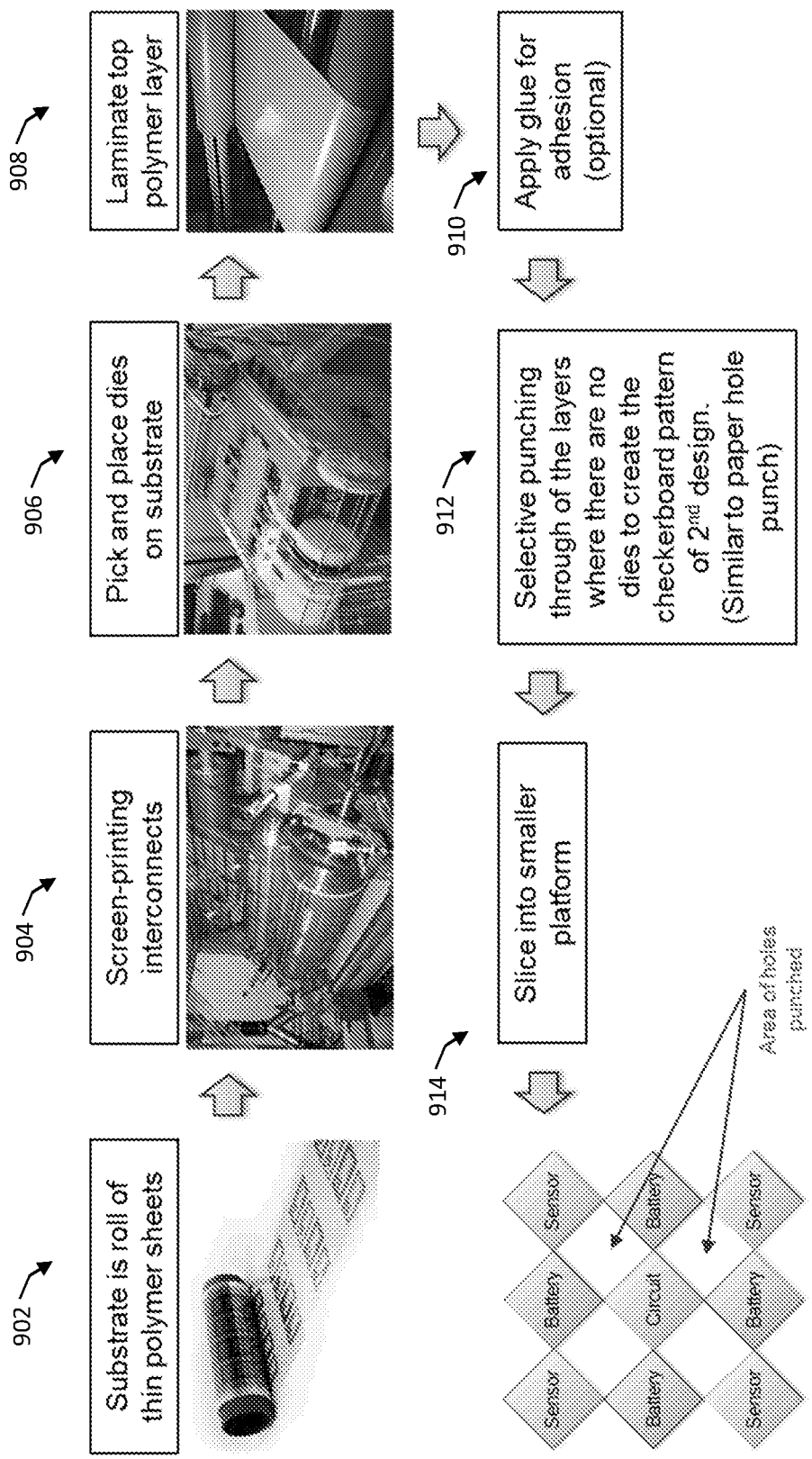
FIG. 9 is a block diagram illustrating an exemplary method of producing a modular flexible deformable platform according to the disclosure.

FIG. 9 illustrates an exemplary process for producing a flexible deformable platform according to the disclosure. At 902, a roll of substrate material is provided. In this embodiment, the substrate material is a roll of thin polymer sheets, but other processes for providing a substrate can be used in other embodiments. At 904, interconnects, i.e., electronic connections to extend between various tiles are printed onto the substrate material. In other words, although the substrate at 904 is a continuous sheet rather than discrete tiles, the interconnects are placed at locations on the substrate with reference to locations on the substrate that are to become discrete tiles. In this embodiment, the interconnects are printed on the substrate material via a screen printing process, but other printing methods are also contemplated. At 906, dies corresponding to components to be placed on particular tiles are selected and disposed on the substrate with reference to corresponding interconnects. Advantageously, the interconnects and components are arranged on the substrate in an arrangement such as those described above that has a tolerance for adherence to irregular surfaces and a tolerance for deformation.

At 908, a layer of flexible material is applied over the substrate and dies. In one embodiment, the flexible material is a polymer, such as a Parylene, that is applied to the substrate and dies via a lamination process. The flexible material can act as a passivation or protection layer, and also includes material that forms the corner connections between the discrete tiles to be formed. Optionally, at 910, an adhesive that enables adhering a platform to a desired location is applied to a rear face of the substrate that is opposite of the layer of flexible material. In one embodiment, a backing sheet is additionally disposed over the adhesive to protect the adhesive until the platform is desirably installed.

At 912, regions of the substrate and layer of flexible material that correspond to gaps between tiles is punched through and removed. Through this process, discrete tiles are formed that are electrically connected via the interconnects and flexibly connected via the flexible material layer at respective corners. In one embodiment, the gaps are arranged in a checkerboard fashion, with the result that when material corresponding to the gaps is removed, a checkerboard tile arrangement as described above is produced.

In one embodiment, components corresponding to a plurality of platforms are placed on a single sheet of substrate. In another embodiment, excess substrate material surrounds a platform formed by the foregoing process. At 914, the substrate is sliced or cut away to release a finished platform(s).

Figure 10:
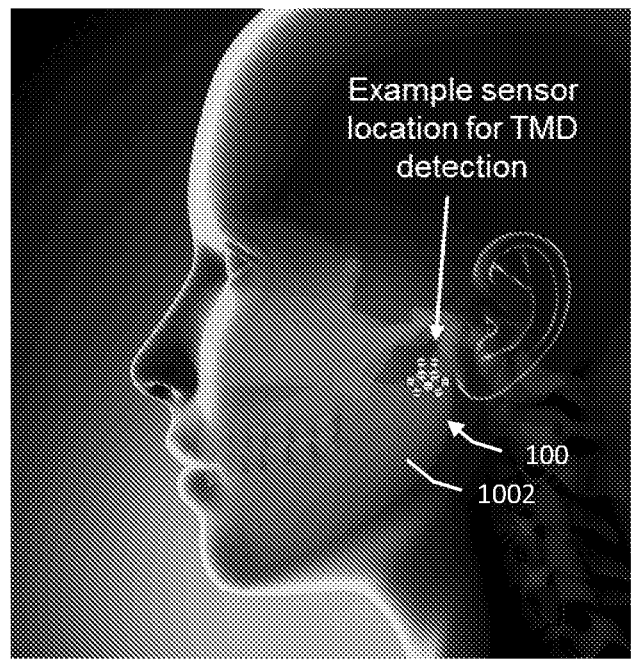
FIG. 10 is an illustration of an exemplary use of the platform adhered to the skin of a user.

FIG. 10 is an image 1000 illustrating an exemplary use of the platform 100. In FIG. 10, the irregular surface is the skin of a user's face 1002. Due to, for example, motion of the user's mouth or neck, and the skin on which the platform 100 is disposed may exhibit deformation. Abrasion, such as when the face moves against a pillow or blanket during sleep, can also produce delaminating forces between the platform 100 and the skin of the face 1002. In order for accurate and efficient use of the platform for various purposes, it is desirable that the platform 100 maintains good contact with the skin. The flexibility and deformation tolerance of the platform 100 as described above enables the platform 100 to maintain good surface contact with the skin, even in the presence of the aforementioned deformation and delamination forces.

One potential uses for a platform 100 disposed on the skin of a user is for the detection of Temporomandibular (TMD) joint dysfunction disorders, which involve pain and or dysfunction of motion for muscles that move the jaw. Such disorders are often difficult to diagnose or quantify, and are difficult to accurately sense using conventional sensors, since the skin around the joint region of the jaw exhibits too much deformation to accurately retain conventional adhesive sensor patches.

Other uses for a platform according to this disclosure include, but are not limited to, sensing muscle movements, monitoring body conditions of a user, sensing an ambient variable such as temperature, humidity, pressure, or toxicity, communicating with other electronic devices, storing or transmitting data, and performing a processing or computing operation. In one embodiment, a platform according to the disclosure is disposed in or on a fabric to form a wearable electronic device. In another embodiment, a plurality of platforms disposed on a user's skin or clothing are configured to work together as a distributed system.

In further exemplary embodiments:

A modular deformable platform includes a plurality of discrete tiles, where adjacent tiles are connected at their respective corners via flexible corner connections. At least one electrical component is disposed on at least one tile.

The arrangement of the tiles in the platform is configured to enable the platform to deform in response to an applied torque. The flexible corner connection is configured to enable tiles to move and/or rotate relative to other tiles in the platform. The flexible corner connections are additionally configured to enable an electrical connection between components disposed on different tiles.

The tiles can include for example motion detection sensors, muscle motion sensors, temperature sensors, humidity sensors, pressure sensors, toxicity sensors, acoustic sensors, bone vibration sensors, vibration sensors, TMD sensors, batteries, photocells, integrated circuits, indicators, antennas, or combination thereof.

A method of producing a modular deformable platform includes disposing connections and components on a substrate in an arrangement with reference to locations of tiles to be formed, and punching holes through the substrate at locations corresponding to gaps between the tiles, and removing the punched material to form the discrete tiles. A layer of flexible material can be applied over the substrate and dies prior to the punching, whereby the flexible material forms corner connections between tiles when material is removed from the gaps.

A method of using a modular deformable platform includes applying the platform to the skin of a user at a location proximate to a front of the user's ear or a joint of the user's jaw. The location of the application of the platform enables sensing of a TMD condition.

A method of using a modular deformable platform includes applying the platform to a wearable article or skin of a user. The method further includes sensing a parameter, sending or receiving a signal via the platform, or processing data.

A method of using a modular deformable platform includes applying the platform to a surface that exhibits deformation, determining a torque acting on the surface with reference to deformation observed in the platform.

While the above embodiments have been described with reference to flexible and deformable electronics, the reader should appreciate that the above-described platform is not limited to electronics. The platform is suitable for a wide variety of flexible articles, for example flexible computing components, flexible displays, radios, medical devices, drug delivery devices, bandages, patches, grafts, and other applications.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the foregoing disclosure.

What is claimed is:

1. A modular deformable electronics platform for supporting electronics on a surface, comprising:
   a plurality of discrete flexible tiles, each tile defining at least one corner, and each tile configured to be separately attached to the surface;
   a plurality of flexible corner connections that connect corners of adjacent members of the plurality of discrete tiles, and that enable the discrete tiles to at least one of translate and rotate relative to each other while maintaining connections between adjacent tiles;
   at least one electrical component disposed on one of the plurality of discrete tiles;
   at least one further electrical component disposed on another of the plurality of discrete tiles; and
   a plurality of interconnects disposed on the plurality of discrete tiles, such that the at least one electrical component is electrically in communication with the at least one further electrical component,
   wherein the plurality of flexible corner connections are positioned such that each flexible corner connection covers a respective set of adjacent interconnects.

2. The electronics platform according to claim 1, wherein:
   each tile includes a base; and
   each interconnect is disposed on the base of a respective tile in a region of the at least one corner, such that interconnects of adjacent tiles are configured to electrically connect the adjacent tiles.

3. The electronics platform according to claim 1, wherein the at least one electrical component includes at least one of a sensor, a battery, an indicator, an antenna, a photocell, and an integrated circuit.

4. The electronics platform according to claim 1, wherein a first subset of the plurality of discrete tiles are extension tiles that do not include an electrical component, the extension tiles distributed radially around a second subset of the plurality of discrete tiles that has at least one electrical component.

5. The electronics platform according to claim 1, wherein each pair of adjacent corner connections defines an axis about which at least a portion of the platform is configured to flex without deformation.

6. The electronics platform according to claim 2, wherein the base includes a Parylene.

7. The electronics platform according to claim 3, wherein the sensor is configured to detect at least one of temperature, humidity, motion, pressure, toxicity, sound, vibrations, and a medical condition of a user.

8. The electronics platform according to claim 5, wherein the plurality of flexible corner connections are formed by a passivation layer disposed over the plurality of tiles, the passivation layer separated into the plurality of flexible corner connections and a discrete layer over each tile via the gaps.

9. A method of producing a modular deformable electronics platform, comprising:
   disposing a plurality of interconnects on a flexible substrate at locations corresponding to an arrangement of discrete flexible tiles;
   disposing at least one die corresponding to at least one electrical component onto the substrate at a location corresponding to one of the discrete tiles, and so as to be electrically connected to the plurality of interconnects;
   disposing at least one further die corresponding to at least one further electrical component onto the substrate at a location corresponding to another one of the discrete tiles, and so as to be electrically connected to the plurality of interconnects;
   applying a layer of flexible material over the interconnects and the at least one die on the substrate;
   forming the discrete tiles by punching out regions of the flexible material and the substrate that correspond to gaps between edges of the discrete tiles, adjacent tiles being electrically connected via the interconnects, and having corners connected via the flexible material; and removing a remainder of the substrate and flexible material surrounding the arrangement of discrete tiles to form a modular deformable electronics platform.

10. The method of claim 9, further comprising:
applying an adhesive to a side of the substrate facing away from the flexible material.

11. The method of claim 9, wherein each pair of adjacent corner connections defines an axis about which at least a portion of the platform is configured to flex without deformation.

* * * * *